(12) United States Patent
Schnell et al.

(10) Patent No.: US 8,035,404 B2
(45) Date of Patent: Oct. 11, 2011

(54) METHOD FOR INFLUENCING SOOT DEPOSITS ON SENSORS

(75) Inventors: Frank Schnell, Gerlingen (DE); Lutz Dorfmueller, Gerlingen (DE); Ralf Schmidt, Gerlingen (DE); Sabine Roesch, Ditzingen (DE); Helmut Marx, Hochdorf (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 632 days.

(21) Appl. No.: 11/629,418

(22) PCT Filed: Apr. 15, 2005

(86) PCT No.: PCT/EP2005/051664
§ 371 (c)(1),
(2), (4) Date: Oct. 23, 2008

(87) PCT Pub. No.: WO2005/124313
PCT Pub. Date: Dec. 29, 2005

(65) Prior Publication Data
US 2009/0051376 A1    Feb. 26, 2009

(30) Foreign Application Priority Data
Jun. 16, 2004 (DE) .......................... 10 2004 028 997

(51) Int. Cl.
*G01R 27/08* (2006.01)
*G01N 27/00* (2006.01)
*G01N 37/00* (2006.01)

(52) U.S. Cl. .................. 324/724; 324/71.4; 73/28.02
(58) Field of Classification Search .......... 324/724, 324/698, 71.4; 73/28.02
See application file for complete search history.

(56) References Cited

U.S. PATENT DOCUMENTS

| 5,215,643 | A  | * | 6/1993 | Kusanagi et al. | ............. 204/412 |
| 5,457,396 | A  |   | 10/1995 | Mori et al. | |
| 6,255,954 | B1 |   | 7/2001 | Brown et al. | |
| 6,553,849 | B1 | * | 4/2003 | Scofield et al. | ............. 73/865.5 |
| 6,949,936 | B2 | * | 9/2005 | Stone et al. | ............. 324/633 |
| 7,543,477 | B2 | * | 6/2009 | Berger et al. | ............. 73/23.33 |
| 7,568,376 | B2 | * | 8/2009 | Strohmaier et al. | ......... 73/23.21 |

FOREIGN PATENT DOCUMENTS

| DE | 198 53 841 | 6/1999 |
| DE | 101 49 333 | 5/2003 |
| JP | 60-014018 | 1/1985 |
| JP | 63-271151 | 11/1988 |
| JP | 04-080648 | 3/1992 |
| WO | 03 006976 | 1/2003 |

* cited by examiner

*Primary Examiner* — Jeff Natalini
(74) *Attorney, Agent, or Firm* — Kenyon & Kenyon LLP

(57) ABSTRACT

A method is described for controlling the soot deposition on sensors. A sensor element is provided, which includes a first electrode and a second electrode. Different measuring voltages $U_1$ and $U_2$ can be applied to the sensor element. During a first time period $t_1$, the sensor element is operated at a higher voltage $U_1$ until a triggering threshold AP of the sensor element is exceeded, while it is operated at a voltage $U_2$, which is different from higher voltage $U_1$, $U_2$ being lower than voltage $U_1$, during a second time period $t_2$.

8 Claims, 4 Drawing Sheets

METHOD FOR INFLUENCING SOOT DEPOSITS ON SENSORS

BACKGROUND INFORMATION

Particle emission requirements for internal combustion engines, in particular compression-ignition internal combustion engines, are becoming increasingly stricter. As the introduction of further standards is being planned, the soot emissions downstream from the internal combustion engine, i.e., downstream from a diesel particle filter, must be monitored during the driving operation. In addition, prediction of the diesel particle filter load is to be provided for determining the soot input and optimizing the regeneration strategy or monitoring regeneration in order to ensure a high degree of system reliability for the diesel particle filter system.

Currently, resistive particle sensors for conductive particles are known in which two or more metallic electrodes are provided, the particles, in particular soot particles, which deposit on these sensors short-circuiting the electrodes meshing in a comb-like manner and thus modifying the impedance of the electrode structure. With increasing particle concentration on the sensor surface, a decreasing resistance, i.e., an increasing current at a constant applied voltage, is thus measurable between the electrodes. Normally a threshold value, a triggering threshold, is defined, and the time of accumulation is assumed as a measure for the deposited soot particle mass. For regenerating the sensor element after the deposition of soot thereon, the sensor element must usually be burned free with the aid of an integrated heating element. The sensor is unable to detect the amount of soot during the phase of being burned free.

German Published Patent Application No. 101 49 333 describes a sensor device for measuring the moisture of gases. A resistance measuring structure cooperating with a soot layer is provided on a substrate; furthermore, a temperature measuring device is provided. The temperature measuring device includes a resistance thermometer and means for measuring a frequency-dependent AC resistance. Furthermore, a heating device is associated with the sensor device. The particle size of the soot particles contained in the soot layer is between 20 nm and 150 mm.

PCT International Published Patent Application No. 03/006976 describes a sensor for detecting particles and a method for checking its function. The sensor is used for detecting particles in a gas flow, in particular for detecting soot particles in an exhaust gas flow. At least two measuring electrodes are situated on a substrate made of insulating material. The measuring electrodes are at least partially covered by a catching sleeve. A heating element is also associated with the sensor. The sensor's particle detecting function, in particular its soot detecting function, is monitored by assigning a capacitor to the measuring electrodes of the sensor and ascertaining the capacitance of this capacitor. When the capacitance of the capacitor differs from the setpoint value, an error message is generated. To burn off the deposited soot particles, the sensor is heated, and afterwards the resistance of the insulation between the measuring electrodes of the sensor is measured. The resistance of the insulation measured after heating the sensor is used as the correcting quantity for operating the sensor.

SUMMARY OF THE INVENTION

The approach according to the present invention makes it possible to influence the deposition rate of particles on the sensor via electronic measures, i.e., variable measures which may be taken during the operation of the sensor. Since the soot concentrations upstream and downstream from the diesel particle filter may differ considerably depending on the technology used, however, cost considerations make identical sensors desirable. The method proposed according to the present invention allows the particular sensors used to be adjusted to the area of use, i.e., whether they are situated upstream or downstream from the diesel particle filter. The method proposed according to the present invention allows the sensitivity range of the sensors to be set to the optimum concentration range, the sensor trigger time to be minimized, and the subsequent measuring time to be maximized. This is achieved by applying different voltages to the sensor. If a higher voltage is selected for operating the sensor, the soot layer builds up more rapidly than for a sensor operating with a lower voltage. In order to have the triggering threshold exceeded as fast as possible and to obtain a rapidly analyzable, i.e., measurable, signal, the sensor is operated at a first, higher voltage $U_1$. Subsequently the system switches over to a second voltage $U_2$ in order to achieve a longer measuring time. During the extended measuring time, the variation of the signal is continuously monitored, and information concerning the occurrence of soot surges may be obtained from the signal gradient. Following the method proposed according to the present invention, first the accumulation time until the triggering threshold is reached, characterized by considerable measuring uncertainties, it is implemented by operating the sensor element using a high voltage, and subsequently the sensor element is operated at a reduced voltage in order to extend the measuring time. Consequently, the measuring uncertainties occurring during the accumulation time have no significant effect.

By taking variable measures, dependent on the location of the sensor, during the operation of the sensor, the deposition rate of soot particles on the sensor and thus the sensitivity range of the sensor may be electronically adjusted for a predefined, fixed sensor design and a predefined, fixed construction regarding installation and application, and thus it may be optimally adapted to the location of the sensor in question. The same sensor may be directly electronically adjusted for different applications, for example, for high soot concentrations or for an on-board diagnosis. The sensor situated in front of the diesel particle filter system is used for detecting the soot mass deposited in the diesel particle filter.

The sensor situated upstream from the diesel particle filter system is used for enhancing the system's reliability and for ensuring operation of the diesel particle filter under optimum conditions. Since those factors depend, to a considerable extent, on the soot mass deposited in the diesel particle filter, accurate measurement of the particle concentration upstream from the diesel particle filter, in particular ascertaining a high particle concentration upstream from the diesel particle filter, is very important.

A sensor installed downstream from the diesel particle filter offers the option of performing on-board diagnosis and is also used for ensuring proper operation of the exhaust gas treatment system.

DETAILED DESCRIPTION

Figure 1:
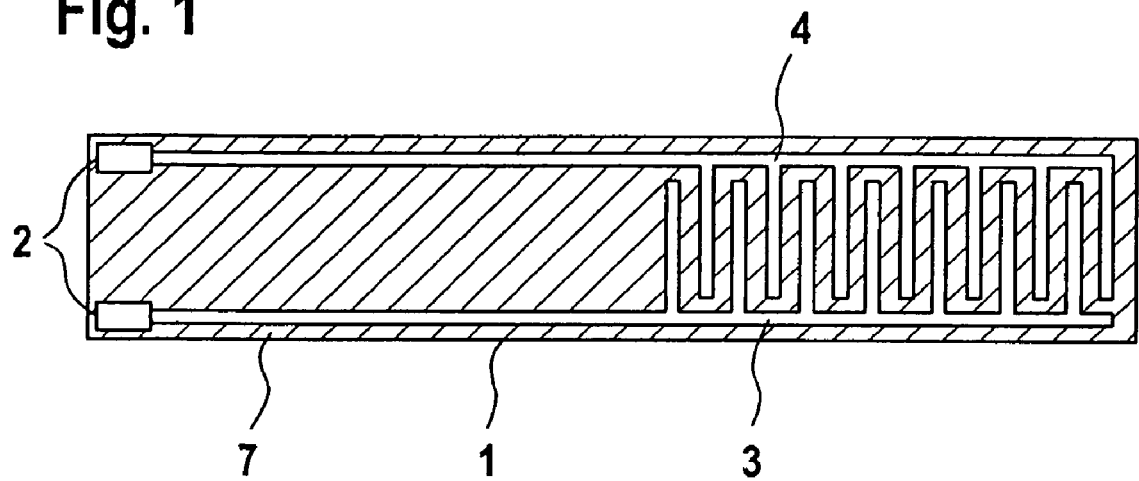
FIG. 1 shows a top view onto a sensor having an electrode structure.

Sensor element 1 includes a substrate 7 used as a support, which may be made of an aluminum oxide ceramic, for example. A resistance measuring structure, having a first comb electrode 3 and a second comb electrode 4, is applied to substrate 7 used as support. The resistance measuring structure including first comb electrode 3 and second comb electrode 4 is used for measuring the electric resistance of a particle layer 5—see the illustration of FIG. 2, which covers first comb electrode 3 and second comb electrode 4 of sensor element 1. When a voltage is applied to voltage terminals 2 of sensor element 1, an inhomogeneous electric field 6 is formed between meshing comb electrodes 3, 4, see the illustration of FIG. 3, where the inhomogeneous electric field 6 is represented by field lines 9.

The particles, in particular soot particles, depositing on sensor element 1 may be considered electric dipoles in the electric field. Inhomogeneous electric field 6 exerts a resulting force on the electric dipole, i.e., in the present case on the soot particles, which are attracted to electrodes 3, 4 and thus deposit thereon as particle layer 5. If the soot particles are charged, they are subject to the effect of an additional force toward electrodes 3, 4 according to the equation $\vec{F} = q \cdot \vec{E}$, and deposit on sensor element 1 (F=force; q=charge; E=intensity of electric field).

If the flow containing the particles passes by sensor element 1 illustrated in FIG. 1, an electric force is exerted on the particles contained in the flow, which is a function of the applied voltage $U_1$, for example, 21 V or $U_2$=10 V. By varying the voltage applied to sensor element 1 at voltage terminals 2, an additional, controllable variable may be imposed on the diffusion-controlled process of soot deposition to influence the mass flow of soot particles onto sensor surface 1.1 of sensor element 1.

This means that, if a higher voltage $U_1$=21 V is applied, the soot layer builds up more rapidly due to the stronger inhomogeneous electric field 6 than when a lower voltage $U_2$, for example 10 V, is applied, creating a weaker inhomogeneous electric field 6.

Figure 2:
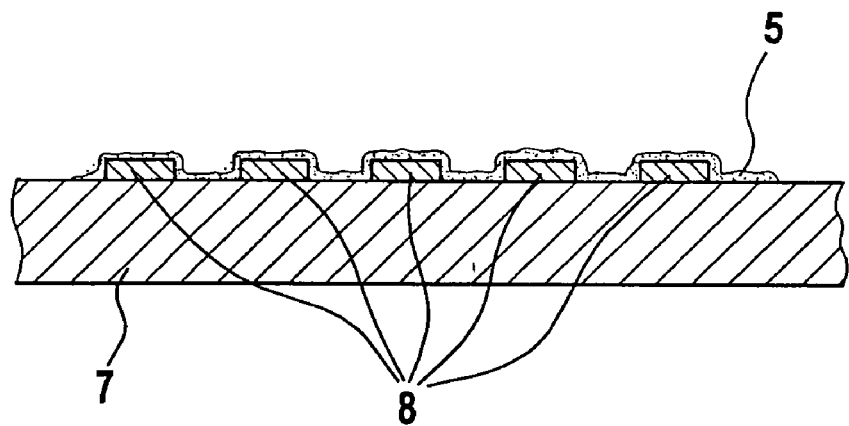
FIG. 2 shows a side view onto the electrode structure applied onto a substrate and covered by a soot particle layer.

FIG. 2 shows the side view of the sensor element according to FIG. 1.

FIG. 2 shows that a soot particle layer 5 has built up above the comb-like meshing electrodes 3 and 4. This layer covers electrodes 3, 4, and 8. If sensor element 1 is operated at an increased voltage $U_1$, for example, 21 V, particle layer 5 builds up more rapidly on the top of comb-like meshed electrodes 3 and 4, and its thickness increases faster compared to operating sensor element 1 at a lower voltage $U_2$.

Figure 3:
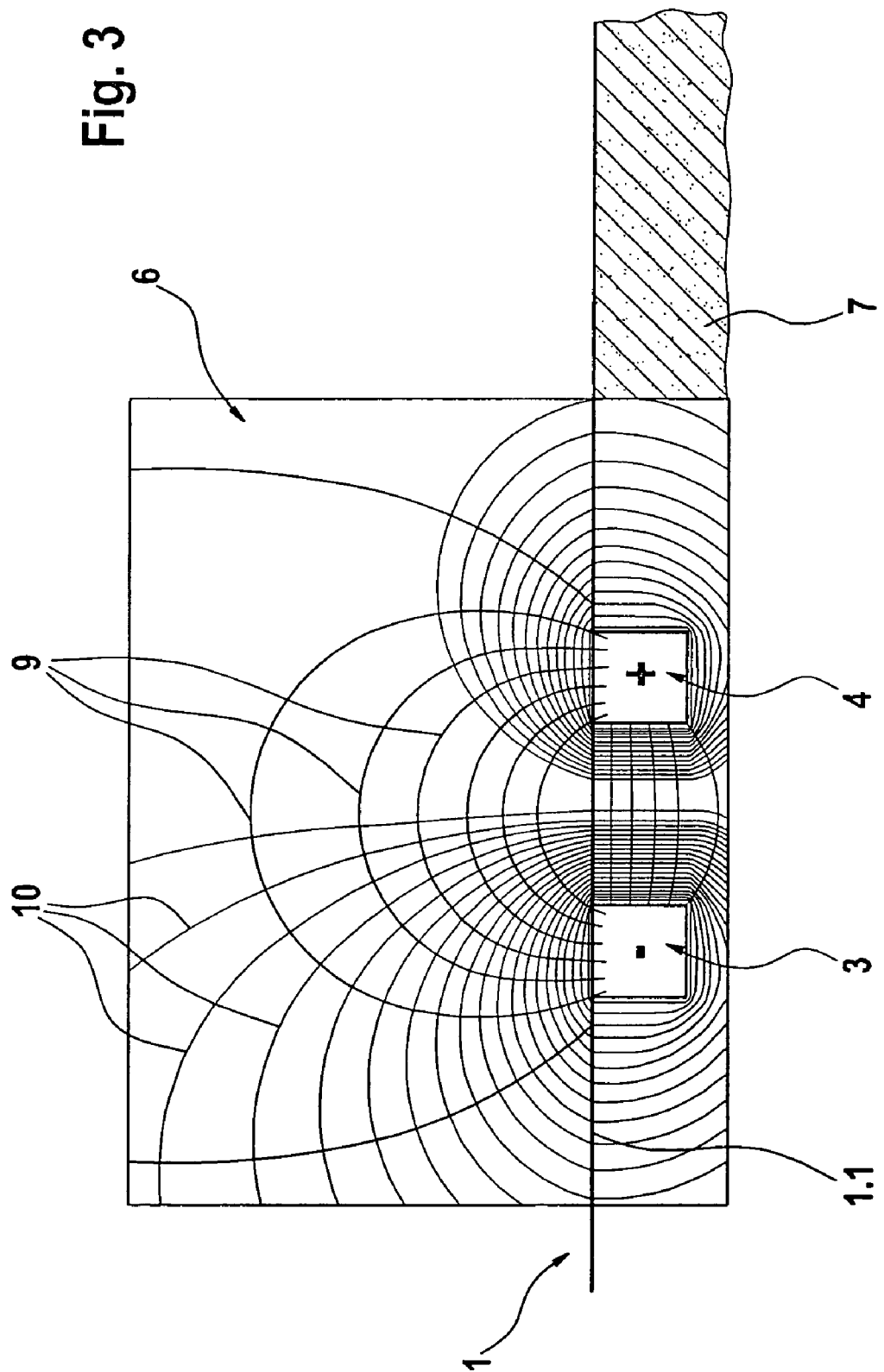
FIG. 3 shows the electric field formed on the electrode structure according to FIGS. 1 and 2.

FIG. 3 schematically shows the inhomogeneous electric field formed, represented by its field lines 9 and equipotential lines 10.

Meshing first comb electrode 3 and second comb electrode 4 are connected to a voltage source, for example, to the vehicle's electric system. Depending on the voltage, either voltage $U_2$ of 10 V, for example, or a higher voltage $U_1$ of 21 V, inhomogeneous electric field 6 illustrated in FIG. 3, represented by field line 9, is formed at meshing first comb electrodes 3 and second comb electrodes 4 above the free spaces therebetween.

Figure 4:
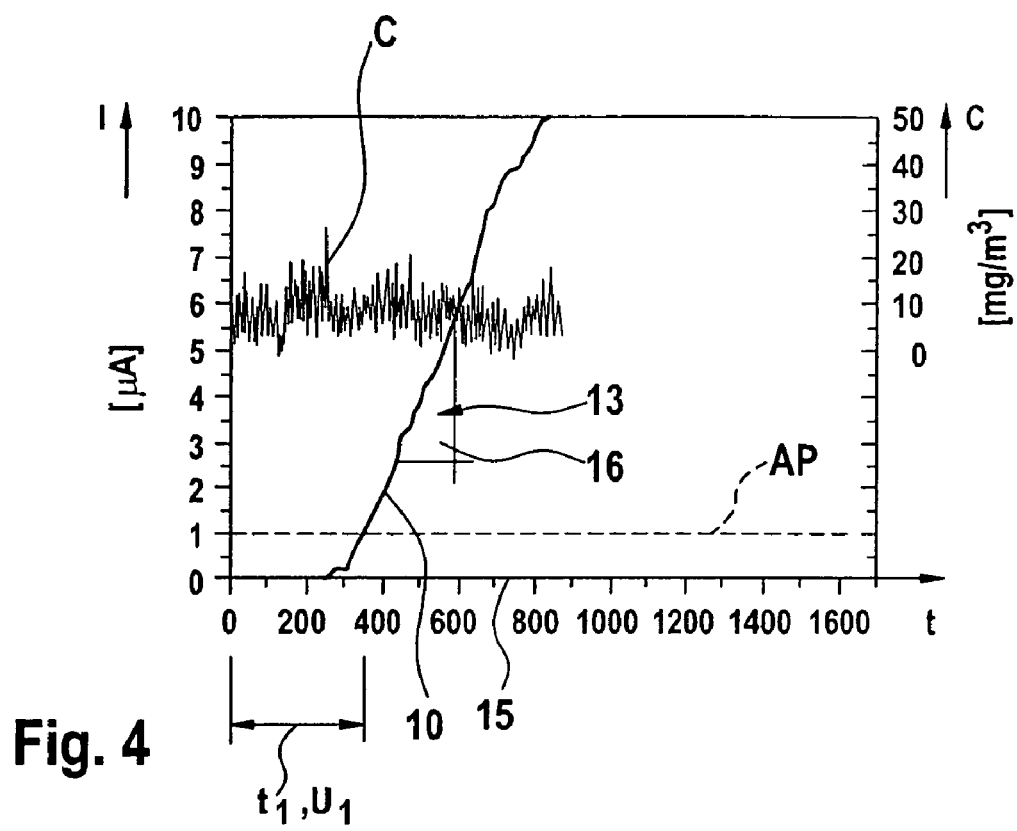
FIG. 4 shows a sensor signal which is established for a first, higher voltage $U_1$, which attains a triggering threshold after a time period $t_1$.
Figure 5:
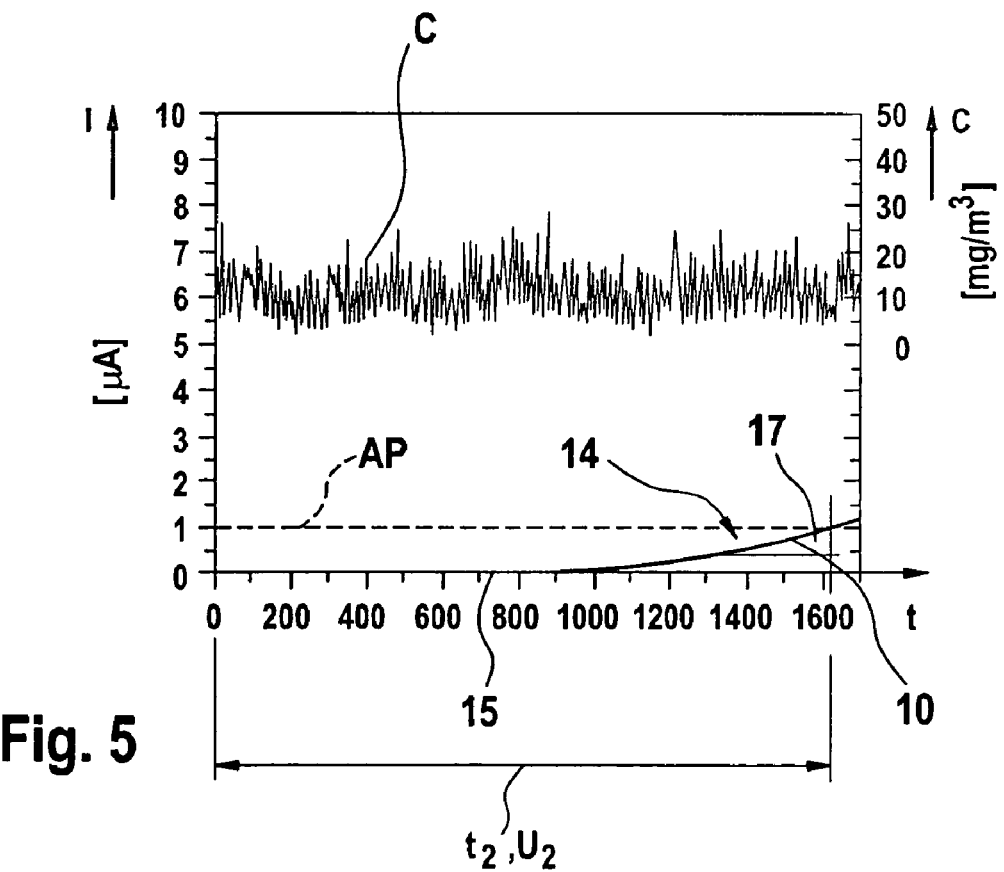
FIG. 5 shows a sensor signal which is established over time for a second, lower voltage $U_2$.

FIGS. 4 and 5 show the triggering of sensor element 1 in operation using a first voltage $U_1$ of 21 V, for example, and in operation using a second voltage $U_2$ of 10 V, for example. In the embodiments of FIGS. 4 and 5 no switchover between the two voltages $U_1$ and $U_2$ has occurred.

Figure 6:
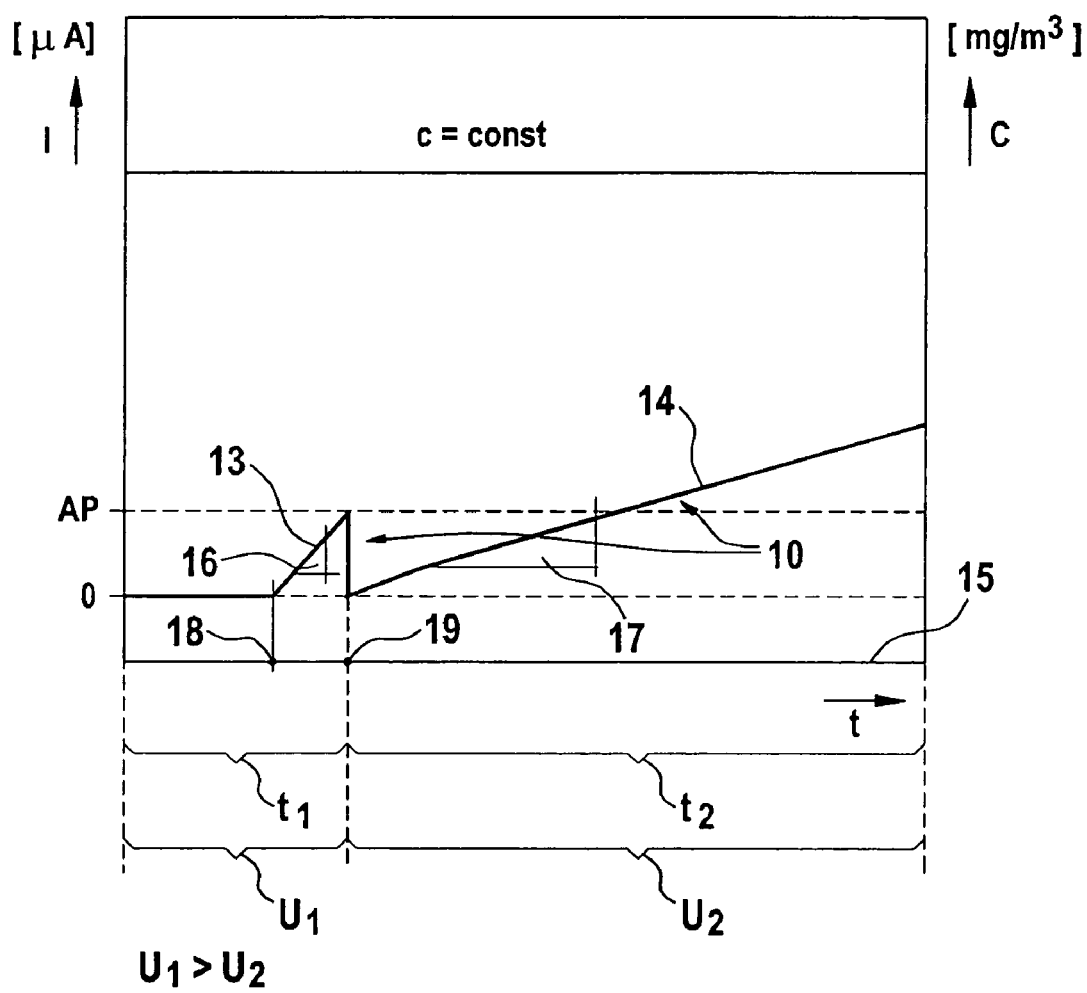
FIG. 6 shows a switchover strategy for the sensor element.

FIG. 4 shows that triggering threshold AP of approximately 1 µA is exceeded by sensor signal 10 after a time period $t_1$. Due to the application of increased voltage $U_1$ of 21 V, for example, sensor signal 10 rapidly increases and exceeds triggering threshold AP after a relatively short time period $t_1$. Triggering threshold AP may be set arbitrarily, also at 2 µA or 3 µA. Due to the increased voltage $U_1$, sensor signal 10 rapidly and steeply increases, which is shown by gradient 16 and by curve 13 of the sensor signal. After reaching measurable currents, i.e., after exceeding triggering threshold AP, direct information on the amount of soot deposited per unit time on surface 1.1 of sensor element 1 may be obtained from gradient 16 and its variation over time axis 15. The operation of sensor element 1 after triggering threshold AP has been exceeded is highly desirable, since errors and cross-influences are visible after triggering threshold AP has been exceeded. After reaching triggering threshold AP after time period $t_1$, the operation of sensor element 1 at increased voltage $U_1$ of 21 V, for example, is switched over to an operation at a lower voltage $U_2$ of 10 V, for example, as depicted in FIG. 6.

Time period $t_1$, during which sensor element 1 is operated at an increased voltage $U_1$, is used for rapidly reaching triggering threshold AP for sensor signal 10, since sensor element 1 delivers no data during time period $t_1$.

The switchover strategy between increased voltage $U_1$ of 21 V, for example, and lower voltage $U_2$ of 10 V, for example, is given by the fact that time period $t_1$ until triggering threshold AP is reached is shortened due to the application of a high voltage $U_1$ and the subsequent time period $t_2$, i.e., the actual measuring time, characterized by visible changes in the signal, is prolonged due to the application of low voltage $U_2$ such as 10 V, for example. This results in a lower particle deposition rate on surface 1.1 of sensor element 1 due to the weaker inhomogeneous electric field 6, due to which a longer time goes by until saturation is attained and sensor element 1 must therefore be regenerated.

FIG. 5 shows that, during time period $t_2$, i.e., the actual measuring time, sensor signal 10 has a flat signal gradient 17; therefore, it does not rise as rapidly as sensor signal 10 according to FIG. 5, when sensor element 1 is operated at a first, increased, voltage $U_1$ of 21 V, for example.

The operation of sensor element 1 according to FIGS. 1 and 2 at an increased voltage $U_1$ of 21 V, for example, during time period $t_1$ and, after switching over, at a voltage $U_2$ of 10 V during second time period $t_2$ was described above. In principle, any voltage generatable in the vehicle's electric system may be used, and the choice of the particular voltage level may be adapted to the particular application. The voltages are preferably between 0 V and 42 V; however, higher voltages are also conceivable. In general, higher voltages are to be preferred up to the point where triggering threshold AP is exceeded, and the voltage is to be switched over to a lower value after triggering threshold AP has been exceeded.

Soot deposition, i.e., buildup of particle layer 5, is influenced by inhomogeneous electric field 6 generating field gradients above the surface of sensor element 1. In addition to the above-described variation of voltages $U_1$, $U_2$ applied to sensor element 1, the structure of first comb electrode 3 and second comb electrode 4 may also be modified. In general, small distances between first comb electrode 3 and second comb electrode 4 result in high field gradients. In addition to the embodiment variants of the electrodes as comb electrodes 3, 4 depicted in FIGS. 1 and 2, they may also have a different design, for example, as linearly shaped electrodes or as electrodes in the shape of a network or a grid, which are contacted underneath a network electrode or grid electrode.

The selection of a suitable electrode layout and the type of electrode surface may also contribute to a local increase in the field intensity. The selection of the electrode layout and the type of electrode surface may be optimally adapted, at the time the sensor is manufactured, to the later application.

FIG. 6 shows that, after time period $t_1$, within which sensor element 1 may be operated at an increased voltage $U_1$ of approximately 21 V, the operating voltage of sensor element 1 is reduced to a lower voltage $U_2$ of 10 V, for example. Sensor element 1 may thus be operated in an optimum operating state, which makes a substantial extension of the measuring time possible after triggering threshold AP has been exceeded. A comparison of time periods $t_1$ and $t_2$ according to FIG. 6 shows that the triggering time may be shortened by applying a high voltage $U_1$ and the measuring time (time period $t_2$) may be extended by applying a low voltage $U_2$.

LIST OF REFERENCE NUMERALS

1 sensor element
1.1 sensor surface
2 voltage terminals
3 first comb electrode
4 second comb electrode
5 particle layer (soot layer)
6 electric field
7 substrate
8 electrodes
9 field line
10 sensor signal [µA]
c soot concentration [mg/m$^3$]
AP triggering threshold
13 curve of sensor signal 10 at $U_1$=21 V
14 curve of sensor signal 10 at $U_2$=10 V
15 time axis
16 signal gradient for $U_1$
17 signal gradient for $U_2$
18 point in time of signal increase
19 point in time of switchover $U_1$ first voltage
20 point in time of switchover $U_2$ second voltage
$t_1$ time period of $U_1$
$t_2$ time period of $U_2$

What is claimed is:

1. A method for controlling a deposition of particles on a sensor element which has a first electrode and a further electrode, comprising:
    applying to the sensor element a first voltage and a second voltage at voltage terminals;
    operating the sensor element at the first voltage during a first time period, a particle layer being rapidly built up on the sensor element during the first time period such that a signal capable of being evaluated is quickly received;
    after a triggering threshold of a resulting current of the sensor element has been exceeded, operating the sensor element at the second voltage during a second time period used as a measuring time, the second voltage being different from zero and less than the first voltage, a signal curve of the resulting current being detected during the second time period; and
    after an expiration of the second time period, regenerating the sensor element.

2. The method as recited in claim 1, wherein the first time period is minimized by the selection of the voltage level of the first voltage.

3. The method as recited in claim 1, wherein the sensor element is operated at the second voltage during the second time period in order to extend the measuring time.

4. The method as recited in claim 1, wherein the first voltage which is applied to the voltage terminals of the sensor element is between 10 V and 42 V.

5. The method as recited in claim 1, wherein the second voltage which is applied to the voltage terminals of the sensor element is between 0 V and 10 V.

6. The method as recited in claim 1, wherein a ratio between the first time period and the second time period is determined by a voltage difference between the first measuring voltage and the second voltage.

7. The method as recited in claim 1, wherein the first and second voltages are group voltages.

8. The method as recited in claim 1, wherein the first and second voltages are applied to an electrode structure in such a way that an inhomogeneous electric field of maximum possible intensity is formed on one surface of the sensor element.

* * * * *